United States Patent [19]

Günther et al.

[11] 4,184,241
[45] Jan. 22, 1980

[54] APPLICATOR FOR AFFIXING A MEMBRANE TO A SENSOR

[75] Inventors: Alphons Günther; Karl-Heinz Pomorin, both of Freiburg; Hans P. Spiess, Umkirch; Georg J. Ullrich, Freiburg, all of Fed. Rep. of Germany

[73] Assignee: Hellige GmbH, Freiburg, Fed. Rep. of Germany

[21] Appl. No.: 869,352

[22] Filed: Jan. 13, 1978

[30] Foreign Application Priority Data

Jan. 18, 1977 [DE] Fed. Rep. of Germany ... 7701259[U]

[51] Int. Cl.² .......................................... B25B 27/14
[52] U.S. Cl. ............................................... 29/278
[58] Field of Search .................. 29/270, 278, 280; 204/195 P

[56] References Cited

U.S. PATENT DOCUMENTS

| 3,835,014 | 9/1974 | Huffhines | 204/195 P |
| 4,050,148 | 9/1977 | Hastings | 29/278 |
| 4,052,788 | 10/1977 | Hastings et al. | 29/278 |

FOREIGN PATENT DOCUMENTS 1058816 6/1959 Fed. Rep. of Germany ............. 29/280

Primary Examiner—James L. Jones, Jr.
Attorney, Agent, or Firm—Norman E. Brunell; W. R. Thiel

[57] ABSTRACT

A device is disclosed for applying a gas permeable membrane to an electrode. A collar is used to hold the membrane on the electrode. The device includes a guide bushing for forcing the collar over the membrane onto the electrode and includes a soft surface for maintaining a constant pressure against the membrane surface during the application.

7 Claims, 1 Drawing Figure

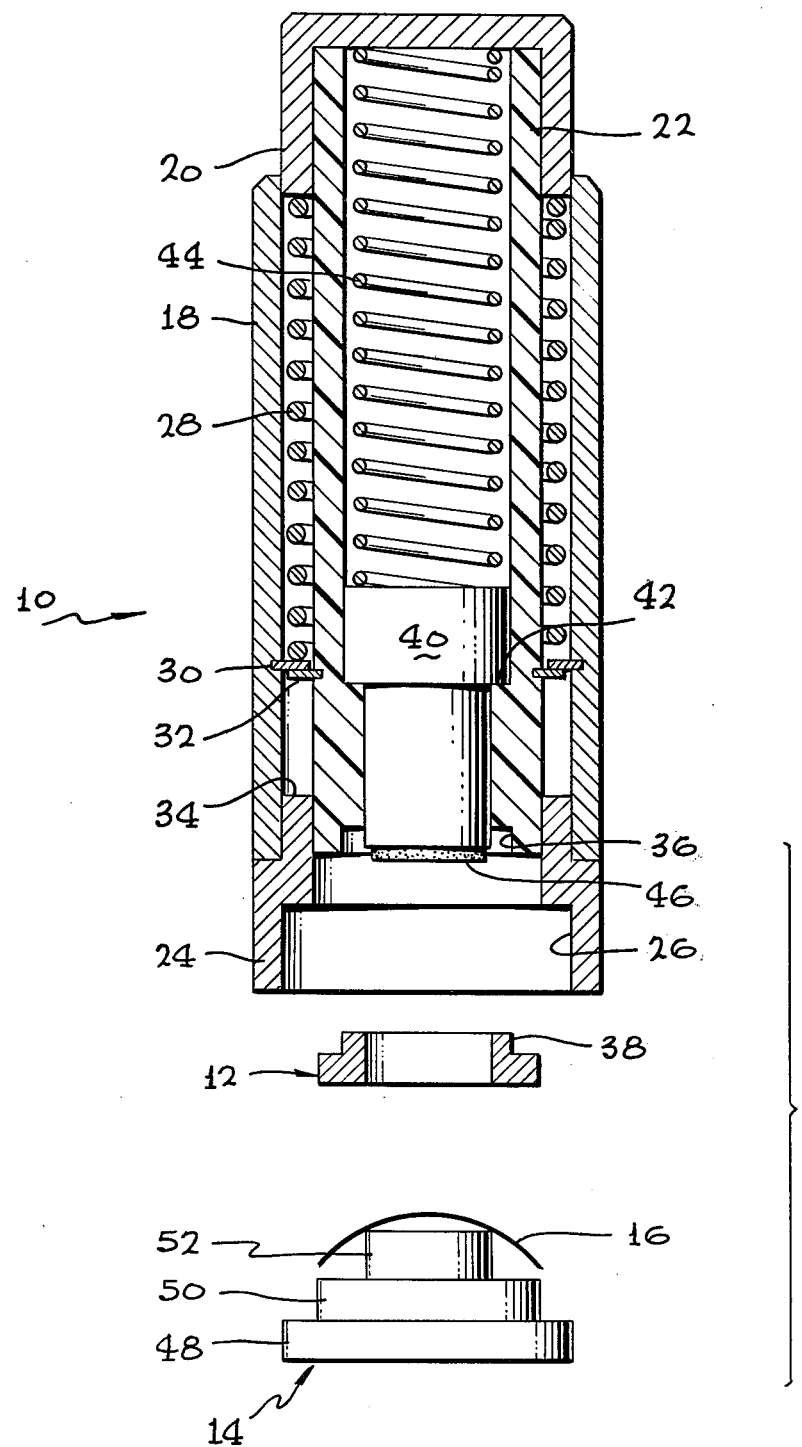

APPLICATOR FOR AFFIXING A MEMBRANE TO A SENSOR

BACKGROUND OF THE INVENTION

1. Field of the Invention

This invention relates to electrochemical electrodes, such as polarographic sensors, which utilize a gas-permeable membrane over the sensing surface. In particular, this device relates to apparatus for applying and affixing the membrane to the electrode.

2. Description of the Prior Art

There are many electrochemical electrodes, such as polarographic sensors, which utilized a gas-permeable membrane between the electrode and the sample. A typical configuration is the well-known Clark Oxygen Polarographic Sensor, which includes an anode and a cathode in the sensor head in contact with an electrolyte and separated from the sample by a membrane permeable to the gas to be measured but impermeable to the electrolyte. Suitable materials for such membranes are plastics such as polyethylene, polypropylene, polytetrafluoraethylene, polyester, silicone rubber and the like.

Many such sensors include a sensing surface of metal or metal imbedded in glass against which the membrane is stretched and attached by a clamping ring. A thin layer of electrolyte is trapped between the sensing surface and the membrane. It is critical to control the thicknesses of the membrane and of the electrolyte layer in order to make the measurements achieved with such electrodes reproducible. It is also necessary to ensure that the attachment of the membrane to the sensing surface by the clamping ring is sufficiently secure to prevent the leakage of any electrolyte to the surrounding medium. Any such leakage could make the attempted measurements useless. Leakage also causes the electrolyte and membrane to dry out too fast.

Controlling the thicknesses and tightness is complicated by the fact that the membranes must be replaced on some electrodes very frequently, as often as every few hours. This is often done in clinical or laboratory surroundings by technicians not specifically trained in this procedure. Reproducibility becomes therefore very difficult to achieve.

One conventional approach is to use a holder which positions the electrode while a membrane can be carefully applied by hand. The unstretched membrane is positioned on the sensor surface and pressed into place by an applicator top. The top is then removed and used, during a second step, to press a retainer ring onto the membrane to hold it in place. This technique has the disadvantage that undesired tensions and/or wrinkles can be produced in the membrane which alter the thickness of the membrane and therefore the electrolyte in an uncontrollable manner and consequently may result in leakage.

Another approach utilizes a cap-shaped membrane as shown in U.S. patent application Ser. No. 805,704, filed June 13, 1977. This cap-shaped membrane is preformed in order to reduce the affects of stretching and stresses on the thickness of the membrane. Achieving reproducibility with these methods, however, is both time consuming and difficult.

SUMMARY OF THE INVENTION

This invention provides for the single step application of a membrane in a manner which results in constant thickness of both the membrane and the electrolyte film.

An applicator device is provided which forces a collar over the membrane and onto the sensor. The applicator provides a soft pad which is pressed against the membrane surface. A spring maintains a constant pressure thereagainst resulting in a constant thickness of the electrolyte film and also the electrode. The device also includes a bushing to guide the collar onto the sensor.

BRIEF DESCRIPTION OF THE DRAWING

The FIGURE shows a device according to the instant invention including a clamping ring or collar and an electrode with an unmounted membrane.

DETAILED DESCRIPTION OF A PREFERRED EMBODIMENT

The FIGURE shows a section along the longitudinal axis of applicator 10, according to the instant invention, shown in exploded view relationship with a clamping ring or collar 12 and sensor 14, upon which membrane 16 has been loosely placed.

Applicator 10 includes main outer housing 18 in the form of a hollow open-ended cylinder. Applicator knob 20 is slideably mounted in housing 18, so that one end thereof protrudes for grasping by the operator. Inner tube 22 is firmly attached to the inner wall of knob 20 at one end and positioned within housing 18. Inner tube 22 may conveniently be made of a rigid plastic which maintains shape stability. The other end of inner tube 22 fits within housing 18. Guide bushing 24 is slideably mounted on one end of inner tube 22 and mounted, at least in part, in housing 18. Guide bushing 24 includes an opening 26, the shape of which is complementary to the shape of sensor 14, as will be described herein below. Return spring 28 is positioned within housing 18 against stop 30 at one end and knob 20 at the other end so that downward actuation of knob 20 compresses spring 28. Boundary ring 32 is fastened to the inner wall of housing 18 at the opposite side of stop ring 30 from spring 28. Boundary ring 32 serves to maintain the assembly including knob 20 and tube 22 within housing 18. Boundary ring 32 serves to restrict the stroke of inner tube 22 within guide bushing 24 so that guide bushing 24 begins to move when ring 32 strikes upper surface 34 of guide bushing 24.

Inner tube 22 includes, at the end mounted within guide bushing 24, a guide in the form of a circular groove 36 which corresponds to the circular boss of surface 38 of collar 12. Compression spring 44 is mounted in inner tube 22 between knob 20 and plunger 40 urging plunger 40 outward therefrom against circular collar surface 42. Positioned on the lower face of plunger 40 is pad 46 made of a soft elastic material, such as gummous plastics, caoutchouc or similar materials.

Sensor 14 includes bottom portion 48, stem 50 and measuring or sensor head 52, which is to be covered by membrane 16, shown resting thereupon. The outer diameter of sensor 52 is just slightly smaller than the inner diameter of collar 12.

The operation of applicator 10 may be described as follows. Clamping ring 12 is first inserted into circular groove 36 of inner tube 22. The outer diameter of plunger 40 is approximately the same size as sensing head 52 and therefore fits within the central opening of collar 12. The upper surface of sensing head 52 is wetted by an electrolyte not shown and membrane 16 is positioned thereupon. Applicator 10 is then positioned upon sensor 14. The outer diameter of stem 50 fits within opening 26. Downward actuation of knob 20 moves inner tube 22 and therefore collar 12 down upon sensing head 52. Pad 18 contacts membrane 60 and presses away any excess of electrolyte while pushing clamping ring 12 over sensing head 52. In this manner, membrane 16 is stretched evenly over sensing head 52 and secured thereon by collar 12. During this procedure, plunger 40 is urged against membrane 16 by compression spring 44 thereby securing an even tension and also assuring a good fit of membrane 16 against sensor 52. When the downward pressure is released from knob 20, spring 28 urges inner tube 22 and circular opening 36 away from collar 12 thereby disengaging applicator 10 from sensor 14.

We claim:

1. An applicator for affixing a membrane to a sensor by means of a clamping ring, comprising:
   a housing member;
   guide means mounted to the housing member for motion relative thereto for urging the clamping ring against the membrane and onto the sensor;
   a return spring for opposing said relative motion;
   a pad; and
   means, mounted for motion with the guide means, for urging the pad against a portion of the membrane not contacted by the clamping ring against the sensor with a constant pressure.

2. The applicator of claim 1, comprising:
   guide bushing means for securing the sensor with respect to the housing member by surrounding the sensor, the guide bushing means including an opening therewith through which the guide means is permitted to move.

3. An applicator for affixing a membrane to a sensor by means of a clamping ring, comprising:
   a housing member;
   guide means mounted to the housing member for motion relative thereto for urging the clamping ring against the membrane and onto the sensor;
   pad means, mounted for motion coaxially within the guide means, for pressing a portion of the membrane not contacted by the clamping ring against the sensor with a constant pressure;
   a plunger mounted for motion coaxially within the tubular guide means, the pad means being mounted on one end of the plunger; and
   a spring in contact with the other end of the plunger for urging the plunger in the axial direction against the sensor.

4. An applicator for affixing a membrane to a sensor by means of a clamping ring, comprising:
   a housing member;
   guide means mounted to the housing member for motion relative thereto for urging the clamping ring against the membrane and onto the sensor, wherein both the housing member and the guide means are generally tubular in shape, the guide means being mounted coaxially within the housing member;
   a return spring mounted coaxially around the guide means and within the housing means for opposing the motion thereof;
   pad means, mounted for motion with the guide means, for pressing a portion of the membrane not contacted by the clamping ring against the sensor with a constant pressure; and
   a compression spring mounted coaxially within the guide means for urging the pad means against the membrane.

5. The applicator of claim 4, comprising:
   a knob mounted on one end of the guide means and extending outside of the housing member for grasping by the operator.

6. An applicator for affixing a membrane to a sensor by means of a clamping ring, comprising:
   a tubular housing having a guide bushing at one end for positioning the sensor;
   a tubular guide member mounted coaxially within the housing having a circular groove surrounding an opening at one end for pressing the clamping ring against the membrane positioned on the sensor;
   a plunger mounted coaxially within the guide member and extending through the opening, the plunger having a soft face for pressing against the membrane within the area surrounded by the clamping ring; and
   a compression spring for urging the plunger face against the membrane with a constant low pressure without regard to the motion of the guide member.

7. The applicator of claim 6 further including:
   a knob mounted on the guide member and extending beyond the housing for manual operation to press the clamping ring against the membrane; and
   a return spring for opposing the motion of the guide member.

* * * * *